(12) United States Patent
Zeltz et al.

(10) Patent No.: US 7,611,871 B2
(45) Date of Patent: Nov. 3, 2009

(54) METHOD FOR THE SPECIFIC DETERMINATION OF DNA SEQUENCES BY MEANS OF PARALLEL AMPLIFICATION

(75) Inventors: Patric Zeltz, Kirchzarten (DE); Stephan Schneider, Freiburg (DE)

(73) Assignee: Biochip Technologies GmbH, Freiburg (DE)

( * ) Notice: Subject to any disclaimer, the term of this patent is extended or adjusted under 35 U.S.C. 154(b) by 284 days.

(21) Appl. No.: 10/363,161

(22) PCT Filed: Sep. 4, 2001

(86) PCT No.: PCT/EP01/10160

§ 371 (c)(1),
(2), (4) Date: Sep. 15, 2003

(87) PCT Pub. No.: WO02/20833

PCT Pub. Date: Mar. 14, 2002

(65) Prior Publication Data

US 2004/0048270 A1 Mar. 11, 2004

(30) Foreign Application Priority Data

Sep. 5, 2000 (EP) .................................. 00119182

(51) Int. Cl.
*C12P 19/37* (2006.01)
*C12Q 1/68* (2006.01)
*C07H 21/02* (2006.01)
*C07H 21/04* (2006.01)
*C12M 1/34* (2006.01)
*C12M 3/00* (2006.01)

(52) U.S. Cl. .................... 435/91.2; 435/6; 435/287.1; 536/23.1; 536/24.3

(58) Field of Classification Search .................. None
See application file for complete search history.

(56) References Cited

U.S. PATENT DOCUMENTS

| 4,683,195 A | 7/1987 | Mullis et al. |
| 5,250,429 A | 10/1993 | Jolly et al. |
| 5,565,318 A | 10/1996 | Walker et al. |
| 6,350,580 B1 * | 2/2002 | Sorge ............................ 435/6 |
| 6,642,000 B1 * | 11/2003 | Strizhkov et al. .............. 435/6 |

FOREIGN PATENT DOCUMENTS

| EP | 0298669 | 1/1989 |
| EP | 0383569 | 8/1990 |

(Continued)

OTHER PUBLICATIONS

Pastinen, T. et al. "Minisequencing: A Specific Tool for DNA Analysis and Diagnostics on Oligonucleotode Arrays", Genome Res., vol. 7, pp. 606-614 (1997).*

(Continued)

*Primary Examiner*—Teresa E Strzelecka
(74) *Attorney, Agent, or Firm*—Griffin & Szipl, P.C.

(57) ABSTRACT

The invention concerns a general method for the specific determination of DNA sequences by means of parallel amplification through nested polymerase chain reaction in a combined liquid-phase/solid-phase-DNA-microarray system, together with modifications derived therefrom to determine, for example, point mutations and to sequence DNA subregions, which according to a particular embodiment can also be unknown.

20 Claims, 5 Drawing Sheets

FOREIGN PATENT DOCUMENTS

| | | |
|---|---|---|
| EP | 0 373 203 B1 | 8/1994 |
| EP | 0 519 338 B1 | 8/1996 |
| EP | 0726310 | 8/1996 |
| EP | 1 186 669 A1 | 3/2002 |
| EP | 1 246 939 | 10/2002 |
| FR | 2674253 | 9/1992 |
| GB | 2333358 | 7/1999 |
| WO | WO 90/11369 | 10/1990 |
| WO | WO 93/09250 | 5/1993 |
| WO | WO 93/14223 | 7/1993 |
| WO | WO 93/21339 | 10/1993 |
| WO | WO 94/16107 | 7/1994 |
| WO | WO 94/17106 | 8/1994 |
| WO | WO 96/04404 | 2/1996 |
| WO | WO 96/17083 | 6/1996 |
| WO | WO 96/26291 | 8/1996 |
| WO | WO 96/31622 | 10/1996 |
| WO | WO 96/32497 | 10/1996 |
| WO | WO 97/32040 | 9/1997 |
| WO | WO 98/00530 | 1/1998 |
| WO | WO 98/28438 | 7/1998 |
| WO | WO 98/36094 | 8/1998 |
| WO | WO 99/05321 | 2/1999 |
| WO | WO 00/43539 | 7/2000 |
| WO | 01/34842 A2 | 5/2001 |
| WO | WO 01/34842 A2 | 5/2001 |

OTHER PUBLICATIONS

Strizhkov et al., "PCR Amplification on a Microarray of Gel-Immobilized Oligonucleotides: Detection of Bacterial Toxin- and Drug-Resistant Genes and Their Mutations," Biotechniques 29:844-857, Oct. 2000, 844-857.

Brenner et al., "Gene Expression Analysis by Massively Parallel Signature Sequencing (MPSS) on Microbead Arrays," Nature Biotechnology, vol. 18, Jun. 2000, 630-634.

Shoffner et al., "Chip PCT. I. Surface Passivation fo Microfabricated Silicon-Glass Chips for PCR," Nucleic Acids Research, 1996, vol. 24, No. 2, 375-379.

Cheng et al., Chip PCT. II. Investigation of Different PCR Amplification Systems in Microfabricated Silicon-Glass Chips, Nucleic Acids Research, 1996, vol. 24, No. 2, 380-385.

Velculescu et al., "Serial Analysis of Gene Expression," Science, vol. 270, Oct. 20, 1995, 484-487.

Neilson et al., "Molecular Phenotype of the Human Oocyte by PCR-SAGE," Genomics 63, 13-24 (2000).

Wordsworth Article, Molecular Immunology Group, Institute of Molecular Medicine, John Radcliffe Hospital, Oxford, UK, 37-39.

Head et al., "Nested Genetic Bit Analysis (N-GBA) for Mutation Detection in the P53 Tumor Suppressor Gene," Nucleic Acids Research, 1997, vol. 25, No. 24, 5065-5071.

Elnifro et al., "Multiplex PCR: Optimization and Application in Diagnostic Virology," Clinical Microbiology Review, Oct. 2000, vol. 13, No. 4, 559-570.

Lockley et al., "Colorimetric Detection of Immobilised PCR Products Generated on a Solid Support," Nucleic Acidse Research, 1997, vol. 25, No. 6, 1313-1314.

Improved methods for nucleic acid amplification, excerpt of EP 0519338B1 (cited above) published Aug. 28, 1996 (Exhibit E).

Extract from the Register of European Patents showing status and recent events in application EP 00990907.8 (WO01/34842) printed on Apr. 6, 2009 from www.epoline.org/portal/public/registerplus (Exhibit G).

Claims submitted Oct. 26, 2007 in application No. EP 00990907.8 (Exhibit H).

Office Action issued Jul. 3, 2008 in application No. EP 00990907.8 (Exhibit I).

Zhang XY, Ehrlich M., Biotechniques, Mar. 1994; 16 (3):502-7 (Exhibit C).

Improved methods for nucleic acid amplification, excerpt of EP 0519338B1 (cited above) published Aug. 28, 1996 (Exhibit E).

Extract from the Register of European Patents showing status and recent events in application EP 00990907.8 (WO01/34842) printed on Apr. 6, 2009 from www.epoline.org/portal/public/registerplus (Exhibit G).

Claims submitted Oct. 26, 2007 in application No. EP 00990907.8 (Exhibit H).

Office Action issued Jul. 3, 2008 in application No. EP 00990907.8 (Exhibit I).

* cited by examiner

Fig. 5

```
GATCGA
 ATCGAT
  TCGATC
   CGATCG
   . . . . . . . . . . . . . . . . . . . .

GATCGATCG . . . . . . . . . . . . . .
```

METHOD FOR THE SPECIFIC DETERMINATION OF DNA SEQUENCES BY MEANS OF PARALLEL AMPLIFICATION

This is a National Phase Application in the United States of International Patent Application No. PCT/EP01/10160 filed Sep. 4, 2001, which claims priority on European Patent Application No. 00 119 182.4, filed Sep. 5, 2000.

FIELD OF THE INVENTION

The present invention concerns a general method for the specific determination of DNA sequences by means of parallel amplification through nested polymerase chain reaction (hereafter also PCR="Polymerase Chain Reaction") in a combined liquid-phase/solid-phase-DNA-microarray system (a solid-phase microarray system of this kind is generally also called a "Biochip" irrespective of the biomolecule actually immobilised thereon [in this case DNA]). Starting from this general method, which as such already enables the detection of particular analytes in a sample that is to be analysed, the present invention equally concerns methods derived therefrom for the determination of point mutations and allelic variants as well as methods to determine the sequence of DNA sub-regions, and indeed even of unknown DNA sub-regions.

BACKGROUND OF THE INVENTION

Within the framework of the present Description, the term "parallel" is used with two different meanings depending on the context. Firstly, for example, the parallel determination of the individual sequence modules mentioned below is possible through the use of different primers, i.e. multiplex operation, and secondly, with specific reference to a method according to the invention, "parallel" amplification means the simultaneous amplification of nucleic acids both in the liquid phase and also in the solid phase by means of $P_3$ primers described according to the invention.

The terms Probe, PCR Primer or Primer as the case may be will be used hereafter depending on the function of the oligonucleotide involved. An oligonucleotide that can be used as a primer for the specific amplification of target sequences can also be used as a probe to detect the target sequence.

A solid-phase microarray system and a method for the analysis of labelled (tagged) DNA sequences by hybridising onto probes immobilised onto a solid support and by determining the localisation of the labelling on the surface is known for example from EP 0 373 203.

A series of individual steps is necessary for a DNA microarray analysis of this kind. Thus the nucleic acid in the samples must be labelled directly or in the form of a copy, or alternatively the operation is performed with a collector nucleic acid on the microarray and a second detection probe in solution. At the same time, many applications such as the detection of biological contamination necessitate the amplification of the sample sequence, for example via a PCR. The (labelled) sample is then hybridised with the probe bonded onto the microarray in order to generate a specific, fixed-position signal which can be recorded and passed on, for example via a detection probe. This procedure gives rise to numerous individual reaction steps that make these analyses labour- and cost-intensive, slow and moreover error-prone.

The performing of a PCR in the presence of a solid support or chip ("PCR on Chip") is in itself already known (Shoffner M. A., Cheng, J., Hvichia G. E., Kricka U., Wilding P.: Chip PCR. I. Surface passivation of microfabricated silicon-glass chips for PCR. Nucleic Acids Res. 1996 Jan. 15; 24(2): 375-9.; Cheng J., Shoffner M. A., Hvichia G. E., Kricka U., Wilding P.: Chip PCR. II. Investigation of different PCR amplification systems in microfabricated silicon-glass chips. Nucleic Acids Res. 1996 Jan. 15, 24(2): 380-5.

The principle of what is called "nested PCR" is also known (cf., for example, C. R. Newton, A. Graham: "PCR", Spektrum Akademischer Verlag Heidelberg Berlin Oxford 1994, p. 59 and the other literature references cited there). Nested PCR involves the use of two PCR primer pairs, of which the members of one pair (known as the outer PCR primers) hybridise upstream and downstream respectively of the target DNA sequence that is to be amplified. The members of the second primer pair (known as the inner PCR primers) hybridise within the section that is pre-determined by the design of the first primer pair. The advantage of this technique lies in the considerable increase in sensitivity and specificity, because the target DNA sequence is amplified preferentially.

However, this technique is extraordinarily sensitive to contaminants of the kind that can be introduced, for example, even by pipetting together the reagents that are needed for the PCR. Moreover, in the case of a nested PCR it is necessary for an amplification that is separate in space and/or time to take place, i.e. for example that either the first amplicon must be diluted or at least one of the outer primers must be removed. Generally the dilution method is used, in which the concentration of the original matrix and the concentration of at least one of the outer primers (hereafter called $P_1$ and $P_2$ respectively) is greatly reduced. Although addition by pipette after the first amplification is possible in principle, it is associated with the risk that the advantages normally inherent in "nested PCR" (see above) will not be achievable. Furthermore, the person skilled in the art knows that when all three primers are present simultaneously in the mixture, no further increase in sensitivity and specificity is achievable, and for this reason it is no longer possible to call it a nested PCR in the real sense either (see for example WO 96/26291). For this reason WO 90/11369, WO 96/31622, WO 93/21339 and WO 98/28438 describe methods in which the amplification cycles take place separated in space and/or time.

Attempts were also made to pre-mix and appropriately stabilise the PCR reagents, particularly in order to simplify the conduct of the PCR reaction. However, there is no description in the state of the art to the effect that the reactants of the intended reaction are provided in dehydrated form directly on a microarray arrangement in such a way that the reaction can be started simply by adding the solution, preferably aqueous, of the sample.

Various different techniques for lyophilising or drying reagents to carry out nucleic acid analyses are described in the state of the art. Thus the preparation of hemispheres with all of the components necessary for a reaction, among them nucleic acids as well, is described in the U.S. Pat. No. 5,565,318. Similar techniques are used in the Applications FR 2 674 253, EP 0 298 669, EP 0 726 310, GB 2 333 358, WO 94/17106, WO 98/00530, U.S. Pat. No. 5,250,429 and EP 0 383 569.

All of the important nucleic acid techniques relating to the use of such reagent spheres are described in concrete terms in the Patent Application WO 96/32497. In addition, an apparatus or equipment in which the dried reagents for a sequencing reaction are used on a plate (presumably a micro-titration plate) is mentioned in the Patent Application WO 94/16107. A solid support in the form of a comb on which these reagents are present and which can be put onto what are known as "8's strips" or micro-titration plates in such a way that the reaction can proceed in the depressions of the micro-titration plates after the release of the reagents is described in Patent Application WO 96/17083.

The application of the individual PCR reagents in the form of spots spatially separated from one another ("Spots") or even application over an area onto a solid phase in the form of a microscope slide is disclosed in Patent Application WO 93/14223. The reversible bonding of dried labelling (tagging) substances and the labelling of a probe after rehydration is also described. However, in this case the probe or probe nucleic acid itself is present expressly reversibly bonded to the solid support.

None of these techniques described in the state of the art enables parallel amplification in a coupled liquid/solid phase PCR system in which the desired results can be generated in a highly specific manner, with a high throughput rate and reproducibly—even in real time if desired—by evaluating an extension product that is formed detectably directly on the solid phase of the system and thus covalently bonded thereto, and can be passed on to the various areas of application.

The task of the invention is to eliminate the deficiencies present in the state of the art and to provide a favourably priced method for the amplification and analysis of DNA sequences that is simple and can be operated free from error, without needing to make any compromises regarding sensitivity and specificity.

SUMMARY OF THE INVENTION

According to the invention, this task is solved by a generally applicable method for the specific determination of DNA sequences by means of parallel amplification in a combined liquid-phase/solid-phase-DNA-microarray system by performing a nested polymerase chain reaction using x PCR primer sets each of at least 3 PCR primers $P_11, P_21, P_31, P_12, P_22, P_32, P_13, P_23, P_33, \ldots P_1x, P_2x, P_3x$, whereby x signifies a natural number (positive integer) and corresponds to the number of DNA sequences to be determined, and whereby for each of the x PCR primer sets (a) two outer PCR primers $P_1, P_2$ are chosen in such a way that they hybridise onto DNA sub-sequences lying upstream and downstream of the target DNA sequence that is to be amplified, (b) one inner PCR primer $P_3$ is chosen in such a way that it hybridises onto a DNA subsequence lying within the target DNA sequence that is to be determined, and is able to form a $P_3$ extension product, and (c) the x outer PCR primers $P_11, P_21, P_12, P_22, P_13, P_23, \ldots P_1x, P_2x$ are present in the liquid phase in excess relative to the x inner PCR primers $P_31, P_32, P_33, \ldots P_3x$, and (d) the x inner PCR primers $P_31, P_32, P_33, \ldots P_3x$ are present irreversibly bonded to a solid phase at x spatially separated defined positions, forming a DNA microarray, and (e) the determination is performed by ascertaining the presence of a $P_3$ extension product at the defined position of the DNA microarray.

Inter alia, the advantages described below are achievable with the method according to the invention. The nested PCR reactions proceed directly and in parallel on the solid phase DNA microarray. The dilution and re-adjustment of the reaction batch after the first PCR using the outer primers $P_1$ and $P_2$ that are usually necessary when carrying out a conventional nested PCR in liquid phase are no longer required. In order to carry out the entire analysis, the user of the method described here is required to perform only one additional operating step, i.e. all that remains for him to do is to add by pipette the sample nucleic acids and the PCR reagents (DNA polymerase and deoxynucleoside triphosphates in PCR buffer), provided that these reagents are not already provided entirely or partially in dehydrated form on the solid support according to a preferred embodiment. This significantly decreases both the labour cost and also the danger of contamination, with a distinct reduction in the opportunities for error.

Thus it is important to achieve the sensitivity of a standard PCR, particularly in the context of applications in which only very small amounts of target DNA are available for analysis. Moreover, it is absolutely essential to guarantee the specificity for the various reaction steps taking place in parallel that is demanded in the case of typical multiplex applications, to exclude both false-positive and false-negative detection events.

Therefore, as stated in detail below, in order to guarantee a combination of these requirements, it is suggested that the operation be performed using at least three primers, whereby only the detection primer $P_3$ is bonded to the solid phase or detection surface and ensures an important selection of the amplicon present in the entire mixture, which is the only thing that makes the required high specificity possible at all. Furthermore this embodiment, which markedly increases the specificity compared to conventional methods, is achieved in that the outer primers $P_1$ and $P_2$ present in the liquid phase are present in excess relative to the detection primers $P_3$ bonded to the solid phase. In other words, the specificity of the detection is ensured in that the only nucleic acid sequences that can participate in the solid phase bonded PCR are those that have previously "qualified" themselves through the outer primers that are also present in the mixture. In the first place this ensures that even the tiniest amounts of target DNA are sufficiently amplified and are thus available for detection. Secondly the concentration differences between the primers $P_1/P_2$ and the primer $P_3$ and the achievability, disadvantaged relative to the liquid phase PCR, of a solid phase bound detection primer for an amplifiable DNA target astonishingly ensure that essentially only nucleic acids that are pre-selected for the target sequence of interest can take part in the detection.

Accordingly, the method according to the invention for the specific determination of DNA sequences by means of parallel amplification through nested PCR in a combined liquid-phase/solid-phase-DNA-microarray system possesses the same sensitivity as a conventional PCR, i.e. one carried out in the liquid phase, and simultaneously a greater specificity than hybridisation assays and primer extension assays. The reason for this is that the specificity with regard to the amplification that is inherent in the primer/sample DNA/polymerase system is additionally enhanced markedly by the specific interaction between the inner PCR primer that is immobilised onto the solid support (and which thus also functions as a probe) and the amplicon. Thus the overall result is a specificity that is superior to that of, for example, a 5-exonuclease assay (e.g. TaqMan™ PCR technology).

These advantages are not achievable using a simple solid phase primer extension assay such as, for example, microtitration plate solid phase PCR (Nunc, cf. for example NucleoLink™) or "Bridge™ PCR" (Mosaic Technologies, cf. for example WO 98/36094 and WO 96/04404).

According to a preferred embodiment of the method of the invention, as a result of the fixed-position inner PCR primers, which also act as probes, it is possible to carry out the operation on the microarray using a labelling (tagging) reagent (for example using labelled nucleotides) in order to investigate numerous different sequences, features or characteristics in parallel.

However, tagging-free detection, for example by using optical or other physical methods, is equally possible, i.e. the method according to the invention can be performed even without labelled nucleotides and the reaction products can be measured.

Here, compared to the conventional hybridisation methods of the state of the art, in which non-specific mass increases on the surface of the solid support constitute a problem, the method of the invention has the advantage that the non-specific mass increase on the surface can be reduced greatly by the use of high temperatures, whereby the covalent bonding of the specific extension products to the solid phase primer $P_3$ ensures an almost exclusive determination of the required specificity.

The measurement of a positionally-specific mass increase can take place for example by physical methods. For example the positionally specific change in the refractive index, the positionally specific change in the electrical resistance and/or electrical conductivity, the positionally specific change in the optical density or even positionally specific dichroic effects etc. can be measured.

Basically the general method according to the invention is suitable for a wide spectrum of areas of application, whereby a distinction can be made between on the one hand the purely diagnostic detection of particular analytes in a sample to be analysed, and on the other hand complex derived modifications of the method to determine sequence data or information about functional relationships in the context of corresponding problems in genomics and/of proteomics. However, this distinction is for purpose of illustration only and should not in any way restrict the basically open applicability of the method according to the invention.

Therefore, according to a particular embodiment, the general method of the present invention comprises a method derived therefrom, in particular to determine point mutations by means of parallel amplification, in which (a) using the method according to the invention defined above, a polymerase chain reaction, through which all of the x variants to be determined are amplified, is carried out, whereby (b) at least $P_3x$ primer families are used, whereby each individual member $P_3x$-N of the primer family differs from each other member with regard to the nucleotide at its 3' terminus, whereby N describes the different nucleotides A, C, G and T, and the annealing temperature of the amplification reaction is chosen in such a way that the desired extension products are formed at only those defined positions of the DNA microarray that are characterized by the presence of the primer that is essentially exactly complementary to the point mutation to be determined, (c) a DNA polymerase without any 3'→5' exonuclease activity is used for amplification, and (d) the determination of the point mutation takes place according to Step (e) of the method of the invention defined above.

Here, the statement "primer that is essentially exactly complementary" means that primers that are hybridised and are accepted as matrixes by the DNA polymerase ("template") are extended, i.e. as a rule all of the nucleotides in the region of the 3' terminus are complementary to the matrix (template).

Furthermore, the general method of the present invention comprises a method derived therefrom for the determination of the sequence of DNA sub-regions by means of parallel amplification in which (a) using the method according to the invention defined above, a polymerase chain reaction, through which all of the x sequences to be determined are amplified, is carried out, whereby (b) at least $P_3x$ primer families are used, whereby each individual member $P_3x$-N, . . . $P_3x$-Nn of the primer family differs from each other member with regard to its 1 to n nucleotides at the 3' terminus, whereby N describes the different nucleotides A, C, G and T, and n indicates the length of the sequence(s) to be determined, and the annealing temperature of the amplification reaction is chosen in such a way that the desired extension products are formed at only those defined positions of the DNA microarray that are characterized by the presence of the primer that is essentially exactly complementary to the sequence that is to be determined, (c) a DNA polymerase without any 3'→5' exonuclease activity is used for amplification, and (d) the detection of the sequence(s) to be determined takes place according to Step (e) of the method according to the invention defined above.

Although the areas of application of the first two derived modifications of the general method of the invention can be entirely different, the determination takes place in essentially the same way. Although the intention in the derived method to determine the sequence of DNA sub-regions is to determine more than merely the terminal 3' nucleotide, as a result of the known design of the microarray and the grouping of the individual reaction regions into fields corresponding to the first, second, third . . . and nth position of the sequence to be determined, the determination of the DNA sub-region takes place by successive read-outs of the data obtained for each field. In other words the field in which, based on the array design, the first base to be determined is detected is evaluated first before, knowing the result from this first field, the determination of the base at the second position of the sequence to be determined is performed, etc. Preferably each examination of a field takes place by recording and assigning the largest measured signal strength. Of course the field measurements can also take place in a parallel manner. Additional reference is made in this context to FIG. 3.

According to another preferred embodiment of the present invention, the general method also comprises a method to determine the sequence of unknown DNA sub-regions by means of parallel amplification in which (a) using the above-defined general method according to the invention, a polymerase chain reaction is carried out through which the sequence of all of the n nucleotides of the sequences to be determined is ascertained, whereby (b) a set of inner primers $P_3$ with a defined length n and encompassing all of the permutations is used, whereby several primers can hybridise exactly with and can form extension products of a defined length with in each case a different region of the sequence to be determined, and each individual one of these primers is situated at a different defined position of the DNA microarray, (c) a DNA polymerase without any 3'→5' exonuclease activity is used for amplification, and (d) the determination of the sequence takes place by ascertaining the extension products formed in Step (b), assigning these determined values to the defined positions of the DNA microarray, and compilation of the sequence to be determined in the context of a combinatorial analysis, computer-assisted if necessary, whereby the actual alignment of the individual data to the overall sequence is performed using the respective overlapping sequence regions.

Alternatively, a consensus PCR can also take place via the ligation of PCR adapters. This achieves a signature sequencing starting from a "pool" of cDNA sequences (which can also be performed quantitatively in the case of on-line observation of the amplification). A sequencing method of this kind (MPSS="Massively Parallel Signature Sequencing") was described recently (Brenner et al., Nature Biotechnology, Vol. 18, June 2000, pages 630-34) and can be carried out in a much simpler way if the technical teaching disclosed in the present document is taken into account. For this purpose, the method according to the invention merely requires the cDNA generation, a restriction digestion and the adapter ligation before the assay. In contrast to this, MPSS requires the production of the cDNA, a restriction digestion, the subsequent hybridising onto "beads", the "FACS" sorting (FACS=Fluorescence-Activated Cell Sorter) of the "beads" and a repetition of the ligation and restriction digestion steps.

The basic steps of sequence determination are known to the person skilled in the art from the general literature on "Sequencing by Hybridisation" technology (cf. for example EP 0 373 203). Moreover, reference is made to FIGS. 4 and 5 to illustrate the method described.

According to an alternative embodiment of this method, the determination of the sequence takes place by ascertaining the respective lengths of the extension products formed in Step (b) and assignment of the values ascertained to the defined positions of the DNA microarray.

According to another preferred embodiment, the method described above can also be used for signature sequencing and quantification, beginning with an unknown sequence, by means of primers having at least 9 nucleotides.

For this purpose, unknown sequences are cut with a restriction enzyme, adapter primers ligated on and the ligation products separated from the remainder of the DNA and amplified on and onto the chip, for example by the use of nonamer primers. For example the cDNAs of a complete bacterial RNA "pool" are determined. The amplicon preferably comprises 18-25 bp (base pairs). The solid phase primers are all 9 nucleotides long and differ in their sequence. There are 262144 different primer variants on the solid phase. Standard PCR conditions are again employed, but after 10-20 cycles the annealing temperature is lowered to 30-50° C. in order to favour the solid phase amplification with the nonamers. Only exactly complementary primers are extended. After staining, the resulting pattern allows the determination of the sequence by comparison with the usual data bases.

Thus the sequence determination of products of the "SAGE" method is enabled (Velculeecu V. E. et al., Science 1995, Vol. 270, pages 484-87; Neilson, L. et al., Genomics 2000, Vol. 63, pages 13-24). The initial amount of the cDNAs can be determined by on-line detection.

Moreover, the present invention concerns a solid phase DNA microarray to carry out a method according to the invention, on which x inner PCR primers $P_31$, $P_32$, $P_33$, ... $P_3x$ are irreversibly bonded to the solid phase at n spatially separated positions.

As a result of the method according to the invention to determine the sequence of DNA subregions by means of parallel amplification, it is possible to eliminate the disadvantages of the sequencing methods of the state of the art, namely inter alia the small sensitivity brought about by the fundamental linearity of a methodology of this kind.

For example, in the case of what is known as "Cycle Sequencing", only one amplification takes place in the liquid phase, with the result that the separation of the sequencing products is necessary, which contains opportunities for errors and is labour-intensive.

On the other hand, in the case of what is known as "Mini Sequencing" (by Sanger's di-deoxy sequencing technique), it is necessary for a large amount of the matrixes or "Template" to be used, since only di-deoxy nucleotides (ddNTPs) are used, and so only a linear amplification takes place.

Compared to the method according to the invention, both of the sequencing techniques described as examples have the disadvantage that a simultaneous, i.e. parallel, amplification of the matrix (template) to be determined is impossible.

Moreover, the method according to the invention is delimited from the known methods, such as the "Sequencing-by-Hybridisation" technique in particular (for example as described in EP 0 373 203) in that it is possible for only relevant regions of a whole amplicon to be sequenced in a specific manner rather than the entire amplicon. In addition, the method enables a simultaneous determination of the sequence of several internal regions of the amplicon.

To determine SNP ("Single Nucleotide Polymorphism") by hybridising or by the use of the ARMS technique ("Amplification Refractory Mutation System"), cf. for example P. Scheinert: Detection of mutations; BioTec Labortechnik, May 6, 1998) the sequence in question must be known. Furthermore, what is called "Faulty Priming" is not recognised. Multiplex operation (performance in parallel by using several different primers) is not possible because of the generation of extension products of the same length, and so separate mixtures are compulsory.

In contrast and in particular, the method according to the invention to determine point mutations by means of parallel amplification has the advantages described below.

The sequences of 3' bases to be ascertained need not be known (but can be). Furthermore it is not necessary for any terminating agents to be used (as in the case of Sanger's di-deoxy sequencing technique) and the parallel determination of the individual sequence modules that differentially characterise the individual different SNP is possible, i.e. multiplex operation.

The sensitivity is very high (1 copy is recognised) because the sequencing is performed with the most minimal amounts of matrix (template) (1 copy is sufficient) with the aid of exponential amplification.

Further advantageous and/or preferred embodiments of the invention are the subject of the subsidiary claims.

The invention is described in detail below, without limitation, on the basis of embodiment examples and by reference to the illustrations shown in the Figures.

BRIEF DESCRIPTION OF THE DRAWINGS

Shown in the Figures are:

Figure 5:
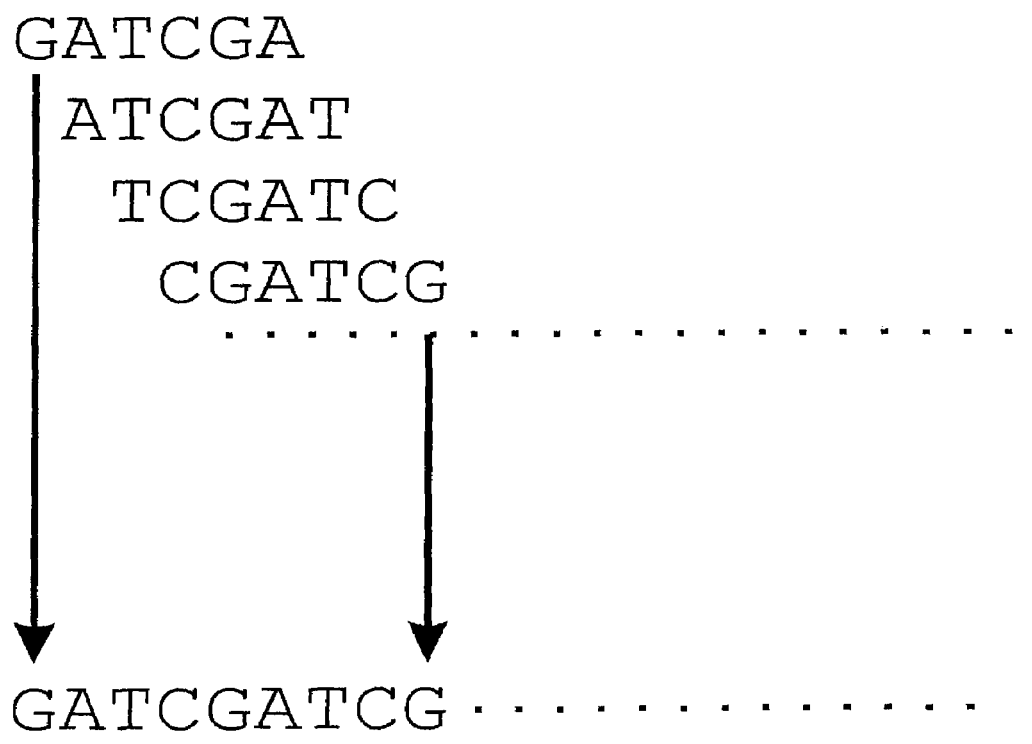

FIG. 5. the collation of the individual results obtained by the signature sequencing according to FIG. 4 to generate a continuous sequence series.

DETAILED DESCRIPTION OF THE INVENTION

Figure 1:
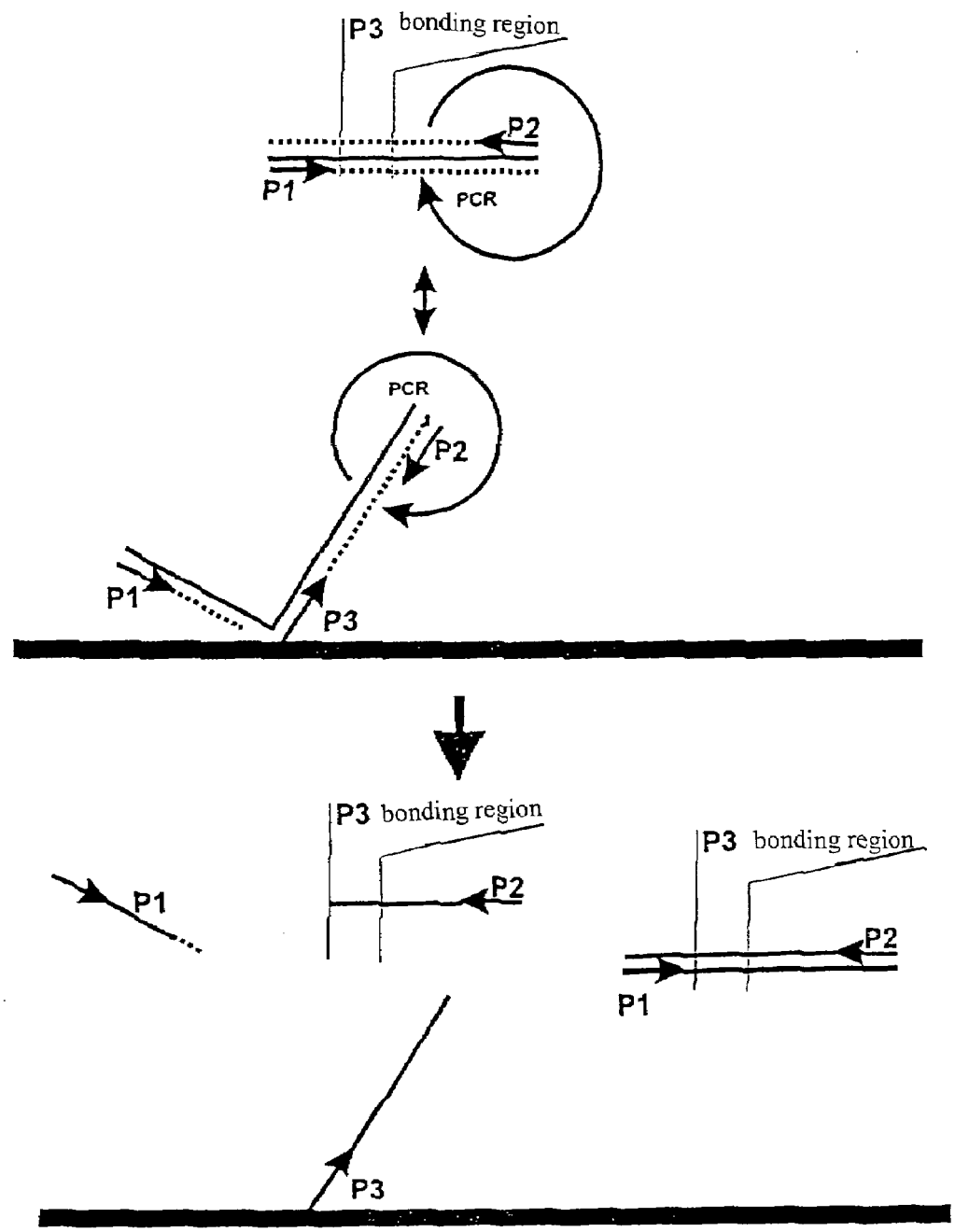
FIG. 1. the specific detection of a known sequence.

In an advantageous configuration of the method of the invention for the specific determination of DNA sequences by means of parallel amplification, the x outer PCR primers $P_11$, $P_21$, $P_12$, $P_22$, $P_13$, $P_23$, ... $P_1x$, $P_2x$ are present in a $10^2$ to $10^{12}$-fold excess, e.g. in a $10^4$-fold excess, relative to the x inner PCR primers $P_31$, $P_32$, $P_33$, ... $P_3x$. As a result, initially the PCR takes place to a greater extent in the liquid phase. However, as the amplicon concentration increases, the PCR takes place increasingly on the solid phase surface, where it corresponds to a nested PCR.

In a further advantageous embodiment of the method of the invention for the specific determination of DNA sequences by means of parallel amplification, the melting temperatures (Tm) of the two outer PCR primers $P_1$ and $P_2$ are different to that of the inner primer $P_3$. For example the outer PCR primers have a higher melting temperature than the inner PCR primer. The course of the reaction can then be adjusted in such a way that first of all at elevated temperature only the outer PCR primers bond or "anneal" and are extended. After the appropriate number of PCR cycles, the temperature is then reduced so that the inner PCR primer too can bond to its "template" and form the extension products required for the determination.

The melting temperatures among the various solid phase primers $P_3$ can also be different. Therefore it is possible to control the reaction in such a way that amplification takes place only at particular defined positions of the DNA microarray. If desired, it is possible by preparing amplification profiles to take into account the different properties of the solid phase primers such as, for example, composition of bases, G-C content and length.

In the method of the invention for the determination of DNA sequences by means of parallel amplification, the solid phase or solid support is not subject to any special restrictions and can be chosen for example from among metal (e.g. aluminium or gold) surfaces, metal surfaces vapour-deposited with $SiO_2$, metal/semimetal oxide (e.g. $Al_2O_3$ or $SiO_2$) surfaces, glass surfaces, polymer surfaces, e.g. in film form, Nylon membranes or nitrocellulose membranes. However, it is clear to the person skilled in the art that basically "semisolid" or gel-like supports are also suitable. The only important factor is that a positional immobilisation and/or spatial localisation of the detection reaction is possible.

For example a suitable gel-like support that is preferred according to the invention can be prepared by immobilising onto a conventional solid support polymerisation initiators that are themselves known and onto which the corresponding monomers can then be polymerised to form what are known as "Polymer Brushes". In the first place these monomers can have functional groups via which it is possible to cross-link the "polymer brushes" to one another, and in the second place they can have functional groups (linker groups) whose purpose is to immobilise probe molecules, e.g. oligonucleotides or antibodies. In the aqueous phase, the layer of "Polymer Brushes" on the surface of the solid support swells in a gel-like manner. With "Polymer Brushes" it is possible to achieve considerably higher graft densities on the support surface than when using conventional self-organising monolayers ("Self-assembled Monolayers", "SAMs") made from bifunctional molecules ("Linkers"). The coupling density with regard to the sample or probe molecules is also considerably higher. Details of the "Polymer Brush" technique are described in WO 00/43539, to which express reference is made at this point.

The use of glass is preferred, since it does not have a porous surface into whose pores the target DNA could diffuse and as a result find its corresponding probe more slowly. Furthermore, glass is mechanically robust, temperature-resistant and insensitive to rigorous washing conditions, and has a low intrinsic fluorescence. All types and kinds of glass are suitable, e.g. quartz glass.

The polymer surface can consist, for example, of polypropylene, polymethylmethacrylate (PMMA) (acrylic glass or Plexiglass) or cycloolefine copolymers (COCs). For example a suitable COC is available from Ticona under the trade name "Topaz".

The exact sequences of the outer and inner primers or probes are chosen by the person skilled in the art in accordance with the actual analytical problem. For example it can involve sequences that hybridise to DNA sequences that are specific to the micro-organisms that are to be detected or differentiated. For example organism-specific sequences can be ascertained by sequence data base comparisons and if necessary "Alignment". Basically there is no limitation to DNA or nucleic acids in general as probes. Because of their known advantages, it is also possible to use DNA-PNA (peptide-nucleic acid) hybrids or chimeras. Modified nucleic acids (e.g. dI, dI-biotin, dU, dU-biotin) can also be used.

According to the invention, the direct or indirect immobilising of the biomolecules, with or without spacers, to the surface of the solid support takes place by covalent bonding and affects equally both the in-situ synthesis of, for example, oligonucleotides as well as the grafting on of previously synthesised nucleotide sequences regardless of the respective length and actual nature of the nucleic acids that act as probes and/or primers.

For example a glass support can be dipped into a solution of bifunctional molecules (known as "Linkers") that have, for example, a halosilane group (e.g. a chlorosilane group) or an alkoxysilane group to couple to the glass surface.

The bifunctional silane that can be used is not subject to any special limitations. All of the silanes that have one, two or three hydrolysable atom(s) or group(s) on the silicon atom come under consideration, for example halogen atoms, $C_1$-$C_4$-alkoxy-, $C_1$-$C_4$-acyloxy- or amino groups.

In concrete terms, for example, isocyanopropyltrimethoxysilane or 3-glycidoxypropyltrimethoxysilane can be applied to a glass support.

The second functional group of the bifunctional silane is also not subject to any special limitations and is chosen depending on the sample or probe molecule (e.g. nucleic acids) that is to be immobilised. Examples include reactive groups that are capable of nucleophilic substitution reactions, nucleophilic addition reactions, Diels-Alder reactions or radical substitution reactions. Actual examples are reactive double bonds, diene groups, dienophile groups, epoxy, aldehyde, hydroxy, carboxylic acid, active ester, amino, disulphide, thiol, aziridine, aziactone, isocyanate, isothiocyanate and azide groups and reactive leaving groups.

These and other bifunctional linkers to couple numerous sample or primer/probe molecules, including in particular those of biological origin, to a plurality of support surfaces are well known to the person skilled in the art, cf. for example "Bioconjugate Techniques" by G. T. Hermanson, Academic Press 1996.

For Nylon membranes it is possible to use, for example, oligonucleotides with an oligo-(dT) tail at the 5' end. The thymine bases of the oligo-(dT) tail are linked covalently to primary amines in the Nylon membrane by UV irradiation.

In a preferred embodiment of a method according to the invention for the specific determination of DNA sequences by means of parallel amplification, all or individual members of the PCR reagents and/or components required for the conduct of the method are present on the solid-phase-DNA-microarray that is used, i.e. the DNA polymerase, e.g. thermostable Taq polymerase (DNA polymerase from *Thermus aquaticus*), suitable buffer substances and all of the deoxynucleoside triphosphates and the x outer primers, stably and reversibly dehydrated onto the surface.

Any desired PCR reagents can be used, for example ordinary commercially available ones. The application to the solid support takes place according to conventional methods, for example by pipetting on. Dehydration, for example by drying in air, in vacuum or in a drying cabinet, over a customary desiccant in a desiccator or by lyophilisation (freeze-drying) takes place afterwards. Lyophilisation is preferred because it involves a particularly quick and gentle dehydration method. The final concentrations can be adjusted easily by applying the PCR reagents in a more concentrated form such that the required reaction parameters such as in particular concentrations and pH are obtained after rehydration in a defined volume of liquid.

The application can also take place in a spatially separated manner.

The PCR reagents are stable on the solid support for a prolonged time, e.g. for at least 6 months, without refrigeration.

Suitably, the inner primers are already covalently bonded or immobilised to the surface of the solid support beforehand (i.e. before applying and dehydrating the PCR reagents).

In use, the sample nucleic acids that may possibly be present in the sample to be analysed are added in aqueous solution, with the result that the PCR reagents rehydrate and, if a "template" complementary sequence anticipated by the design of the analytical starting materials is present, the amplification proceeds on the solid support without the need to add further reagents.

According to a preferred embodiment, analysis/detection takes place with the aid of labelled (tagged) DNA sequences formed covalently as extension products on the solid-phase-DNA-microarray, and by determining the localisation of the labelling on the surface, as known for example from EP 0 373 203.

For example a fluorochrome can be incorporated into the amplicon as a label, whose fluorescence emission is then detected or measured. Since the incorporation of the labelling takes place in a fixed-position manner, the labelling reactions can be detected and/or observed, even in real time if required.

The labelling and detection techniques are not subject to any special restrictions. For example it is possible to use nucleotides labelled radioactively or by fluorescence. In this respect fluorescence labelling has the advantage that it is not necessary to adopt any special protective precautions as when working with radioactive material. The detection of the hybridisation can then take place for example by confocal laser scanning microscopy.

A further possibility is the use of digoxigenin-labelled specific probes (oligonucleotides). In this case the detection of the hybridising can take place for example by a subsequent antibody and colour reaction, e.g. using a poly- or monoclonal digoxigenin antibody, which is conjugated for example with alkaline phosphatase. The alkaline phosphatase converts, for example, nitroblue-tetrazolium chloride (NBT) or 5-bromo-4-chloro-3-indolyl phosphate (BCIP) to form a blue dyestuff.

In a further embodiment, the solid-phase-DNA-microarray suggested for carrying out one of the methods of the invention is present in the form of what is known as a "Lab-on-a-Chip" system in which all of the devices necessary to mix the reactants as well as for temperature control, including if necessary a control unit for all of the devices or some of them, are built into the microarray. A system of this kind, which is basically suitable for use according to the invention, is described for example by Kohler et al. in transcript Laborwelt, No. 2 (2000), pp. 5 ff. "Chip Thermocycler" and can easily be configured and operated without unreasonable expense by the person skilled in the art with a knowledge of the present invention. Alternatively the control of the required process parameters can take place entirely or partially externally, e.g. in a computer equipment.

Summarised briefly, the general method according to the invention for the specific determination of DNA sequences by means of parallel amplification through nested PCR in a combined liquid-phase/solid-phase-DNA-microarray system and the derivatives thereof modified for certain areas of application combine together the sensitivity of the PCR, the parallelism of microarray analysis and the specificity of the primer/"template"/polymerase system with the advantage of the stable dehydrated attachment of reagents to a microarray.

The present invention will be explained in detail below based on the following Examples and by reference to the attached Figures. However, attention is drawn expressly to the fact that the purpose of the Examples is merely to illustrate particular individual embodiments of the present invention, and they should not be interpreted as a limitation of the general inventive idea. Numerous modifications and optimisations of the actual embodiment examples can be carried out by the person skilled in the art without departing from the scope of protection of the present invention, which is defined solely by Subsidiary claims.

EXAMPLE 1

FIG. 1: Specific detection of a known sequence. The upper half of the Figure shows diagrammatically the processes during amplification, and the lower half shows the situation at the time of detection. At least 1 solution primer pair ($P_1$ and $P_2$) and at least 1 solid phase primer ($P_3$) are present. $P_3$ has its bonding region within the amplicon that is amplified by $P_1$ and $P_2$. Since denaturing at 90-95° C. takes place after each cycle, which corresponds to extreme washing steps (stripping), only the covalently bonded reaction products remain on the solid phase after the completion of the reaction (cf. FIG. 1 below). All of the other reaction products are present in the supernatant and are ignored during detection.

The present example concerns the specific detection of the presence of a known sequence, characteristic of Salmonellae, in a foodstuff sample that is to be analysed. The preparation of the sample material takes place in conformity with DIN Instruction 10135 which concerns specifically the detection of Salmonellae.

The sample DNA, dissolved in 100 μl of aqueous solution, is pipetted onto a microarray of activated glass on which all of the other reactants are already present in lyophilised form, whereby all of the components except the $P_3$ primers covalently bonded to the solid phase are reversibly immobilised.

As a result of adding the sample solution, the lyophilised components are rehydrated and are available in the following concentrations for the subsequent progress of the reaction. The primers $P_1$ and $P_2$ are present at concentrations of 100 nM and 600 nM respectively, while the primer $P_3$ has a concentration of 50 pM. The usual PCR standard buffer components of 50 mM of KCl, 10 mM of Tris/HCl, 1.5 mM of $MgCl_2$ and the three nucleotides dATP, dCTP and dGTP, each at a concentration of 200 μM, are present in the aqueous sample solution, which has a pH of 8.3. The dTTP concentration of the system is 75 µM and that of the biotind-UTP is 50 µM. The system also comprises 6.4 units of Taq Polymerase (AmpliTaq™-Gold, Perkin-Elmer).

The reaction is started by activating the polymerase for a period of 10 minutes and proceeds at an annealing temperature for the time being of 65° C. and a denaturing temperature for the time being of 94° C. for 50 cycles, whereby each cycle using a PTC 200 Thermocycler (MJ Research) comprises the following incubation times: 45 seconds at 94° C., 60 seconds at 65° C. and 120 seconds at 72° C.

After the reaction, the biotin incorporated into the covalently bonded products is stained in a known way by means of streptavidin-fluorochrome conjugate and is conveyed to a detection procedure.

EXAMPLE 2

Figure 2:
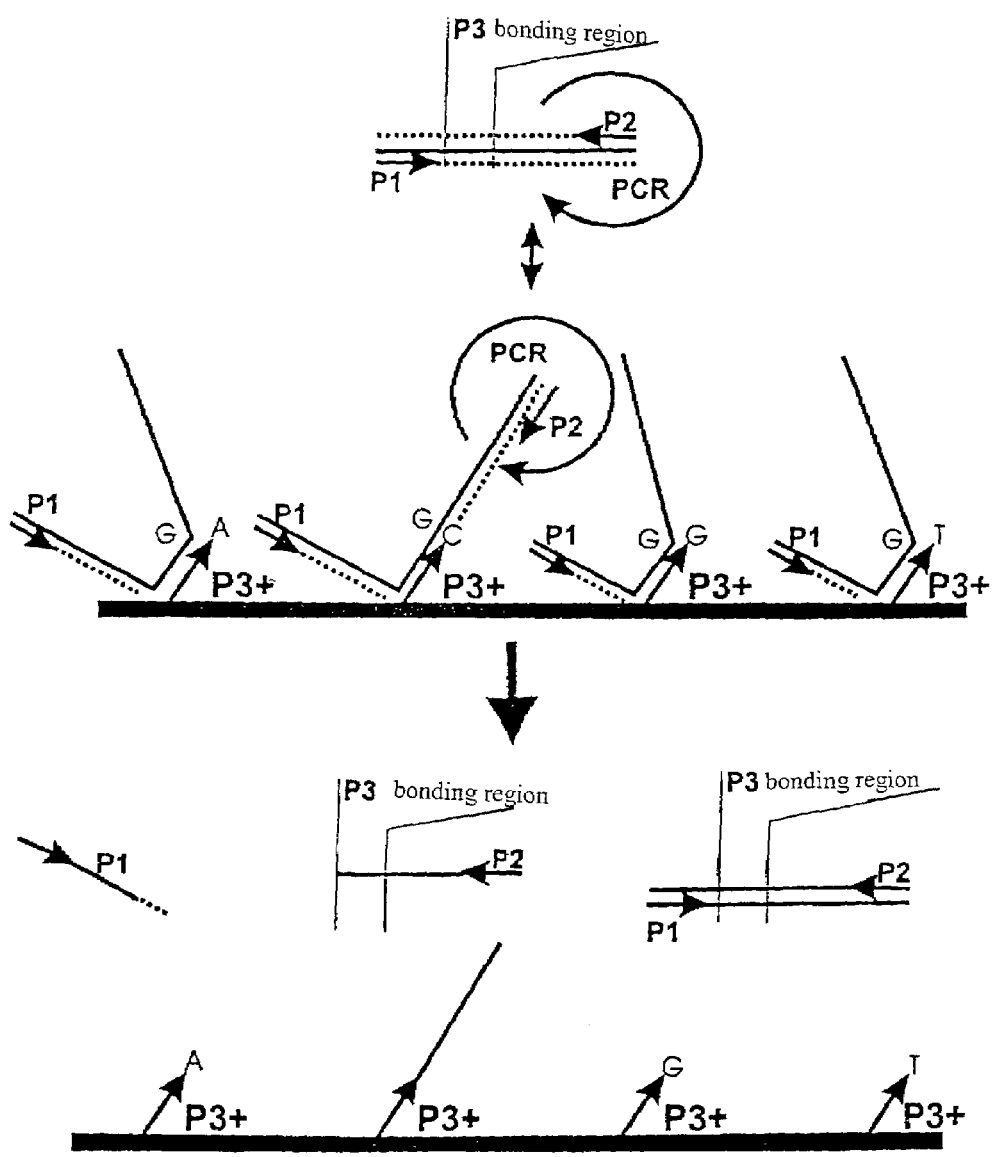
FIG. 2. an allotype determination by the specific determination of the identity of a 3'-terminal nucleotide by means of primer families.

FIG. 2: Allotype determination: Specific determination of the identity of a 3'-terminal nucleotide by means of primer families. The upper half of the Figure shows diagrammatically the processes during the amplification, the lower half the situation at the time of detection.

A Consensus PCR is performed under the reaction conditions stated in Example 1 (cf. for example P. Wordsworth, "Techniques used to define human MHC antigens: polymerase chain reaction and oligonucleotide probes", *Immunol. Lett.* 1991 Jul.; 29(1-2): 37-9) in which all of the 300 variants of the Exon II of the DR gene (HLA Class II), which comprises a total of 270 nucleotides, are amplified. The internally bonding solid phase primers P3 have lengths of from 18 to 27 nucleotides and are members of a total of 250 families, this number being required in order to enable unambiguous identification of one genotype via redundancies, even in the presence of heterozygosity, whereby each individual member of the primer family differs from each other member with respect to the nucleotide at its 3' terminus (cf. FIG. 2).

Because of the essentially identical length of the primers present, the annealing temperature of the amplification reaction is 65° C., and so under the chosen conditions the desired extension products are formed preferentially only at those defined positions of the DNA microarray that are characterized by the presence of the primer that is essentially exactly complementary to the variant sequence that is to be determined.

Following the detection according to Example 1, the fluorescence pattern obtained is compared with the signal pattern permutations to be expected on the basis of the individual sequences of the various different alleles. The matches discovered by the comparison in each case enable the unambiguous identification of the genotype variants that are to be examined.

EXAMPLE 3

Figure 3:
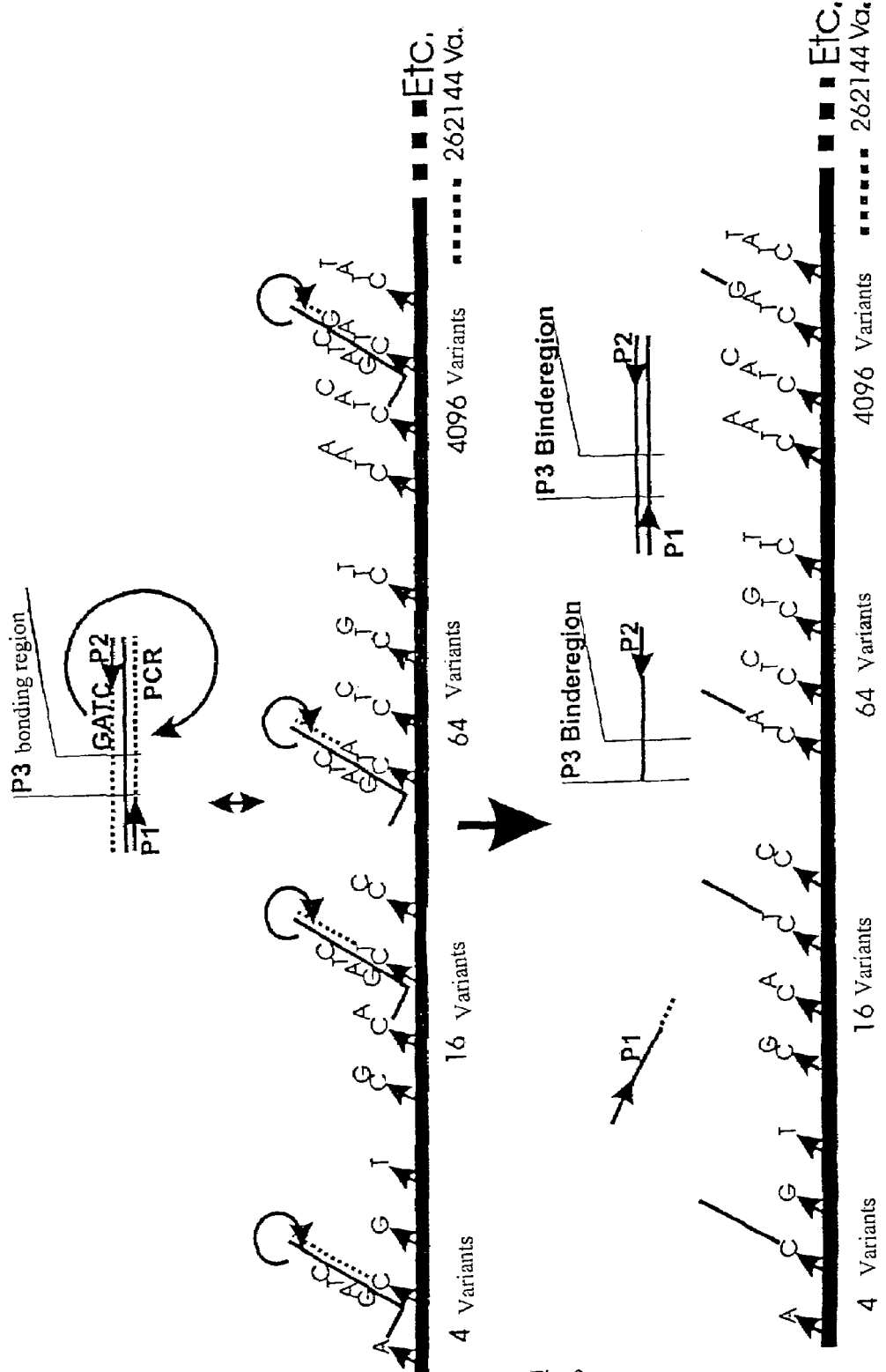
FIG. 3. what is known as "Sequence Tag Acquisition", i.e. a specific signature sequencing starting from a known primer sequence by means of primer families.

FIG. 3: "Sequence Tag Acquisition": Specific signature sequencing beginning with a known primer sequence by means of primer families. The upper half of the Figure shows diagrammatically the events during the amplification, and the lower half shows the situation at the time of detection. In contrast to FIGS. 1 and 2, the side-reactions on the solid phase are not shown in the upper half for reasons of clarity.

A consensus PCR is performed as in Example 2. In this case the 16S-rDNA of an unknown bacterium is amplified. In this case the amplicon has a length of approx. 1200 bp (base pairs). However, the intention is to sequence only an internal region of 6 nucleotides in a variable, i.e. non-conserved region. This unknown sequence section is determined starting from a conserved region. Solid phase primer families differing in each case, starting from a conserved region, by only the last base at the 3' terminus are used for this purpose, yielding a total of $4^6$ which is equivalent to 4096 variants (cf. FIG. 3). The annealing temperature and the total length of the primer are matched to the required specificity (see Example 2). As stated in Example 2, the primers have lengths of between 18 and 27 nucleotides.

Detection takes place as described previously in Example 2.

The evaluation of the data obtained takes place based on the microarray design. As a result of the grouping of the individual reaction regions into fields predetermined by the design, which correspond to the first, second, third, fourth, fifth and sixth positions of the sequence to be determined, the determination of the DNA sub-region comprising 6 nucleotides takes place by the successive read-out of the data obtained for each field. In other words the field in which, based on the array design, the first base to be determined is detected is evaluated first before, knowing the result from this first field, the determination of the base at the second position of the sequence to be determined is performed, etc. Preferably each examination of a field takes place by recording and assigning the largest measured signal strength. Of course the field measurements can also take place in a parallel manner. Additional reference is made in this context to FIG. 3.

EXAMPLE 4

Figure 4:
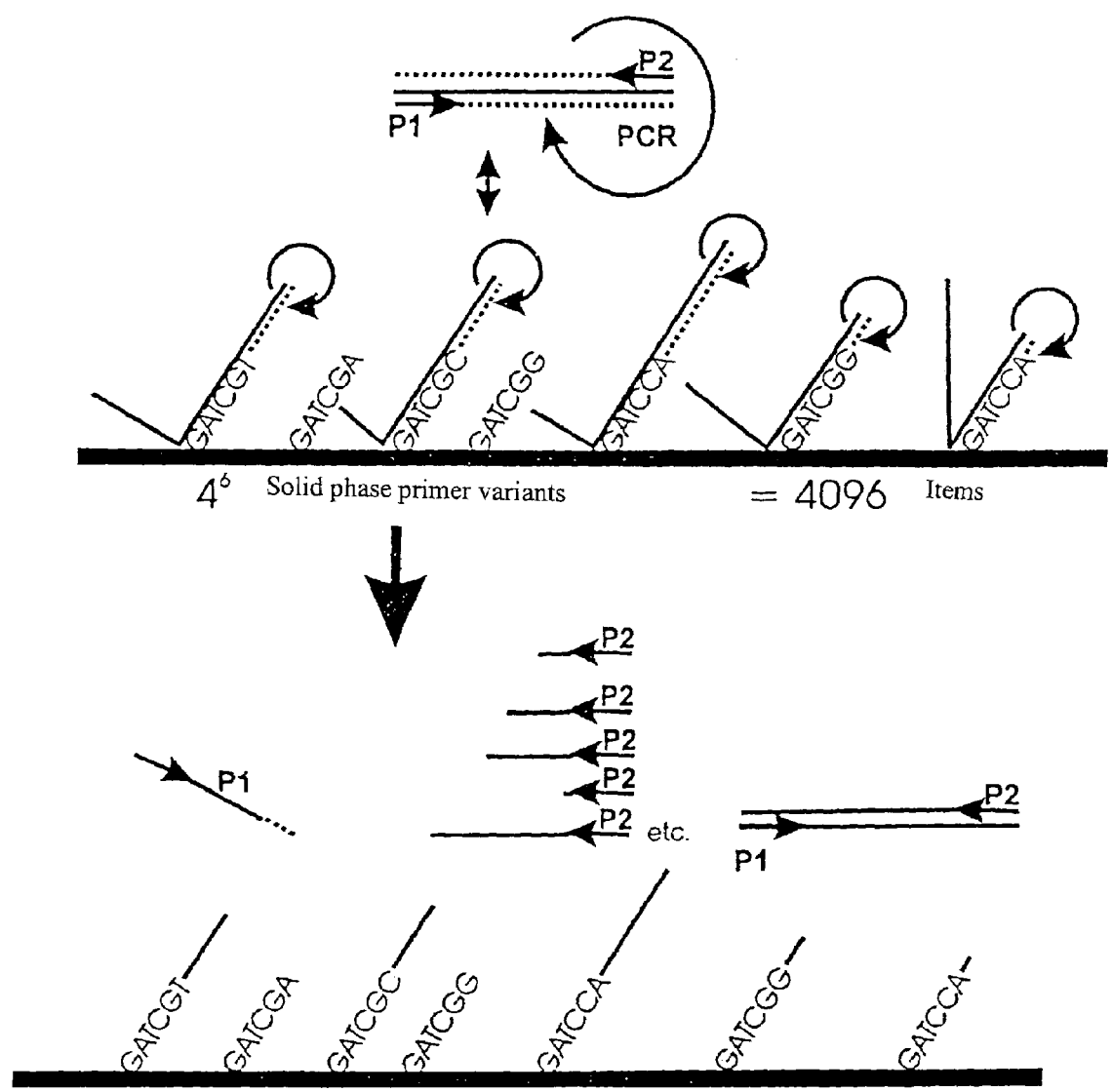
FIG. 4. a signature sequencing starting from an unknown sequence by means of primer hexamers.

FIG. 4: Signature sequencing starting from an unknown sequence by means of primer hexamers. The upper half of the Figure shows diagrammatically the events during the amplification, and the lower half shows the situation at the time of detection. In contrast to FIGS. 1 and 2, the side-reactions on the solid phase are not shown in the upper half for reasons of clarity.

An unknown sequence is amplified by means of specific primers after inverse PCR. Inverse PCR is known in the state of the art (cf. for example C. R. Newton, A. Graham: "PCR", Spektrum Akademischer Verlag Heidelberg Berlin Oxford 1994, pp. 120 ff. and the other literature references cited there). In this case the "border" sequence of an integrated transgene construct in the maize (corn) kernel genome is determined. The amplicon comprises 500 bp (base pairs). The solid phase primers $P_3$ are all 6 nucleotides long and differ in their sequence. There are 4096 different solid phase primer variants on the chip. 1000 copies of the maize DNA are used. Standard PCR conditions are again used (see above). However, the annealing temperature is reduced to 30° C. after cycle 20 in order to favour solid phase amplification with the hexamers.

Afterwards the determination of the sequence takes place by ascertaining the extension products that are formed specifically, assignment of these determined values to the defined positions of the DNA microarray, and compilation of the sequence to be determined in the context of a combinatorial analysis, computer-assisted if necessary, whereby the actual alignment of the individual data to the overall sequence is performed using the respective overlapping sequence regions.

What is claimed is:

1. Method for the specific determination of DNA sequences by means of parallel amplification in a combined liquid-phase/solid-phase-DNA-microarray system by performing a nested polymerase chain reaction using x PCR primer sets each of at least 3 PCR primers $P_1 1, P_2 1, P_3 1, P_1 2, P_2 2, P_3 2, P_1 3, P_2 3, P_3 3, \ldots P_1 x, P_2 x, P_3 x$, whereby x signifies a positive integer and corresponds to the number of DNA sequences to be determined, and whereby for each of the x PCR primer sets (a) two outer PCR primers $P_1$, $P_2$ are chosen in such a way that they hybridise onto DNA sub-sequences lying upstream and downstream of the target DNA sequence that is to be amplified, (b) one inner PCR primer $P_3$ is chosen in such a way that the one inner PCR primer $P_3$ hybridises onto a DNA subsequence lying within the target DNA sequence that is to be determined, and is able to form a $P_3$ extension product, and (c) the x outer PCR primers $P_1 1$, $P_2 1$, $P_1 2$, $P_2 2$, $P_1 3$, $P_2 3$, ... $P_1 x$, $P_2 x$ are present in liquid phase in excess relative to the x inner PCR primers $P_3 1, P_3 2, P_3 3, \ldots P_3 x$, and (d) the x inner PCR primers $P_3 1$, $P_3 2$, $P_3 3$, ... $P_3 x$ are present irreversibly bonded to a solid phase at x spatially separated defined positions, forming a DNA microarray; the method comprising the steps of:

(1) providing the x PCR primer sets;

(2) performing simultaneous amplification, involving a nested polymerase chain reaction, using said primers in both the liquid and solid phase in order to produce a $P_3$ extension product irreversibly bonded to the solid phase, wherein the x outer PCR primers $P_1 1, P_2 1, P_1 2, P_2 2, P_1 3, P_2 3, \ldots P_1 x, P_2 x$ in the liquid phase are present in a $10^2$ to $10^{12}$ -fold excess relative to the x inner PCR primers $P_3 1, P_3 2, P_3 3, \ldots P_3 x$ in the solid phase; and (3) ascertaining the presence of the $P_3$ extension product at one or more defined positions of the DNA microarray.

2. A method according to claim 1 for determining point mutations by means of parallel amplification, in which (a) a polymerase chain reaction, through which all of the x variants to be determined are are amplified, is carried out, whereby (b) at least $P_3 x$ primer families are used, whereby each individual member $P_3 x$-N of the primer family differs from each other member with regard to the nucleotide at its 3' terminus, whereby N describes the different nucleotides A, C, G and T, and the annealing temperature of the amplification reaction is chosen in such a way that the desired extension products are formed at only those defined positions of the DNA microarray that are characterized by the presence of the primer that is essentially exactly complementary to the point mutation to be determined, (c) a DNA polymerase without any 3'→5' exonuclease activity is used for amplification, and (d) the determination of the point mutation takes place according to Step (e) of claim 1.

3. A method according to claim 1 for the determination of the sequence of DNA sub-regions by means of parallel amplification in which (a) a polymerase chain reaction, through which all of the x sequences to be determined are amplified, is carried out, whereby (b) at least $P_3 x$ primer families are used, whereby each individual member $P_3 x$-N, ... $P_3 x$-Nn of the primer family differs from each other member with regard to its 1 to n nucleotides at the 3' terminus, whereby N describes the different nucleotides A, C, G and T, and n indicates the length of the sequence(s) to be determined, and the annealing temperature of the amplification reaction is chosen in such a way that the desired extension products are formed at only those defined positions of the DNA microarray that are characterized by the presence of the primer that is essentially exactly complementary to the sequence that is to be determined, (c) a DNA polymerase without any 3'→5' exonuclease activity is used for amplification, and (d) the detection of the sequence(s) to be determined takes place according to Step (e) of claim 1.

4. A method to according to claim 1 to determine the sequence of unknown DNA sub-regions by means of parallel amplification in which (a) a polymerase chain reaction is carried out through which the sequence of all of the n nucleotides of the sequences to be determined is ascertained, whereby (b) a set of inner primers $P_3$ have a defined length n and encompassing all of the permutations, whereby several primers can hybridise exactly with and can form extension products of a defined length with in each case a different region of the sequence to be determined, and each individual one of these primers is situated at a different defined position of the DNA microarray, (c) a DNA polymerase without any 3'→5' exonuclease activity is used for amplification, and (d) the determination of the sequence takes place by ascertaining the extension products formed in Step (b), assigning these determined values to the defined positions of the DNA microarray, and compilation of the sequence to be determined in the context of a combinatorial analysis, computer-assisted if necessary, whereby the actual alignment of the individual data to the overall sequence is performed using the respective overlapping sequence regions.

5. Method according to claim 1, whereby the melting temperatures of the two outer PCR primers $P_1$ and $P_2$ are different from the melting temperature of the inner primer $P_3$.

6. Method according to one of the foregoing claims, whereby the solid phase is chosen from the group consisting of metal surfaces, metal surfaces vapour-deposited with $SiO_2$, metal/semimental oxide surfaces, glass surfaces, polymer surfaces, nylon surfaces and nitrocellulose membranes.

7. Method according to claim 6, whereby the metal surface is made of aluminium or gold, the metal/semimetal oxide surface is made of $Al_2O_3$ or $SiO_2$, the glass surface is made of quartz glass and the polymer surface is made of polypropylene, polymethylmethacrylate or cycloolefine copolymers.

8. Method according to claim 7, whereby the x inner PCR primers $P_3 1$, $P_3 2$, $P_3 3$, ... $P_3 x$ are bonded to a metal/semimetal oxide surface or glass surface via a bifunctional silane that has one, two or three hydrolysable atom(s) or group(s) on the silicon atom.

9. Method according to claim 8, whereby the hydrolysable atoms or groups comprise halogen atoms, $C_1$-$C_4$-alkoxy-, $C_1$-$C_4$-acyloxy- or amino groups.

10. Method according to claim 8, whereby the second functional group of the bifunctional silane can take part in nucleophilic substitution reactions, nucleophilic addition reactions, Diels-Alder reactions or radical substitution reactions.

11. Method according to claim 10, whereby the second functional group of the bifunctional silane involves a reactive double bond, diene group, dienophile group, epoxy, aldehyde, hydroxy, carboxylic acid, active ester, amino, disulphide, thiol, aziridine, azlactone, isocyanate, isothiocyanate or azide group or reactive leaving group.

12. Method according to claim 1, whereby the x outer PCR primers $P_1 1, P_2 1, P_1 2, P_2 2, P_1 3, P_2 3, \ldots P_1 x, P_2 x$ are present in a $10^4$ -fold excess relative to the x inner PCR primers $P_3 1$, $P_3 2$, $P_3 3$, ... $P_3 x$.

13. Method according to claim 9, whereby the second functional group of the bifunctional silane reacts to take part in nucleophilic substitution reactions, nucleophilic addition reactions, Diels-Alder reactions or radical substitution reactions.

14. Method for the specific determination of DNA sequences by means of parallel amplification in a combined liquid-phase/solid-phase-DNA-microarray system by performing a nested polymerase chain reaction using x PCR primer sets each of at least 3 PCR primers $P_11, P_21, P_31, P_12, P_22, P_32, P_13, P_23, P_33, \ldots P_1x, P_2x, P_3x$, whereby x signifies a positive integer and corresponds to the number of DNA sequences to be determined, and whereby for each of the x PCR primer sets (a) two outer PCR primers $P_1, P_2$ are chosen in such a way that they hybridise onto DNA sub-sequences lying upstream and downstream of the target DNA sequence that is to be amplified, (b) one inner PCR primer $P_3$ is chosen in such a way that the one inner PCR primer P3 hybridises onto a DNA sub-sequence lying within the target DNA sequence that is to be determined, and is able to form a $P_3$ extension product, and (c) the x outer PCR primers $P_11, P_21, P_12, P_22, P_13, P_23, \ldots P_1x, P_2x$ are present in liquid phase in excess relative to the x inner PCR primers $P_31, P_32, P_33, \ldots P_3x$, and (d) the x inner PCR primers $P_31, P_32, P_33, \ldots P_3x$ are present irreversibly bonded to a solid phase at x spatially separated defined positions, forming a DNA microarray; the method comprising the steps of (1) providing the x PCR primer sets;

(2) performing simultaneous amplification, involving a nested polymerase chain reaction, using said primers in both the liquid and solid phase in order to produce a $P_3$ extension product irreversibly bonded to the solid phase, wherein the x outer PCR primers $P_11, P_21, P_12, P_22, P_13, P_23, \ldots P_1x, P_2x$ in the liquid phase are present in a $10^2$ to $10^{12}$-fold excess relative to the x inner PCR primers $P_31, P_32, P_33, \ldots P_3x$ in the solid phase; and (3) ascertaining the presence of the $P_3$ extension product at one or more defined positions of the DNA microarray, wherein the solid phase, to which the x inner PCR primers $P_31, P_32, P_33, \ldots P_3x$ are irreversibly bonded, is a surface.

15. Method according to claim 1, wherein nucleotides used to produce the $P_3$ extension product are labeled radioactively or by fluorescence so that ascertaining the presence of the $P_3$ extension product involves detecting radioactivity or fluorescence of the $P_3$ extension product.

16. Method according to claim 15, wherein confocal laser scanning microscopy is used to detect the $P_3$ extension product.

17. Method according to claim 14, wherein nucleotides used to produce the $P_3$ extension product are labeled radioactively or by fluorescence so that ascertaining the presence of the $P_3$ extension product involves detecting radioactivity or fluorescence of the $P_3$ extension product.

18. Method according to claim 17, wherein confocal laser scanning microscopy is used to detect the $P_3$ extension product.

19. Method for the specific determination of DNA sequences by means of parallel amplification in a combined liquid-phase/solid-phase-DNA-micro array system by performing a nested polymerase chain reaction using x PCR primer sets each of at least 3 PCR primers $P_11, P_21, P_31, P_12, P_22, P_32, P_13, P_23, P_33, \ldots P_1x, P_2x, P_3x$, whereby x signifies a positive integer and corresponds to the number of DNA sequences to be determined, and whereby for each of the x PCR primer sets (a) two outer PCR primers $P_1, P_2$ are chosen in such a way that they hybridise onto DNA sub-sequences lying upstream and downstream of the target DNA sequence that is to be amplified, (b) one inner PCR primer $P_3$ is chosen in such a way that the one inner PCR primer $P_3$ hybridises onto a DNA sub-sequence lying within the target DNA sequence that is to be determined, and is able to form a $P_3$ extension product, and (c) the x outer PCR primers $P_11, P_21, P_12, P_22, P_13, P_23, \ldots P_1x, P_2x$ are present in solution in excess relative to the x inner PCR primers $P_31, P_32, P_33, \ldots P_3x$, and (d) the x inner PCR primers $P_31, P_32, P_33, P_3x$ are present irreversibly bonded to a solid phase at x spatially separated defined positions, forming a DNA microarray; the method comprising the steps of (1) providing the x PCR primer sets;

(2) performing simultaneous amplification, involving a nested polymerase chain reaction, using said primers in both the solution and the solid phase in order to produce a $P_3$ extension product irreversibly bonded to the solid phase, wherein the x outer PCR primers $P_11, P_21, P_12, P_22, P_13, P_23, \ldots P_1x, P_2x$ in the solution are present in a $10^2$ to $10^2$-fold excess relative to the x inner PCR primers $P_31, P_32, P_33, \ldots P_3x$ in the solid phase; and (3) ascertaining the presence of the $P_3$ extension product at one or more defined positions of the DNA microarray, wherein the solid phase, to which the x inner PCR primers $P_31, P_32, P_33, \ldots P_3x$ are irreversibly bonded, is a non-porous surface.

20. Method for the specific determination of DNA sequences by means of parallel amplification in a combined liquid-phase/solid-phase-DNA-microarray system by performing a nested polymerase chain reaction using x PCR primer sets each of at least 3 PCR primers $P_11, P_21, P_31, P_12, P_22, P_32, P_13, P_23, P_33, \ldots P_1x, P_2x, P_3x$, whereby x signifies a positive integer and corresponds to the number of DNA sequences to be determined, and whereby for each of the x PCR primer sets (a) two outer PCR primers $P_1, P_2$ are chosen in such a way that they hybridise onto DNA sub-sequences lying upstream and downstream of the target DNA sequence that is to be amplified, (b) one inner PCR primer $P_3$ is chosen in such a way that the one inner PCR primer $P_3$ hybridises onto a DNA sub-sequence lying within the target DNA sequence that is to be determined, and is able to form a $P_3$ extension product, and (c) the x outer PCR primers $P_11, P_21, P_12, P_22, P_13, P_23, P_1x, P_2x$ are present in solution in excess relative to the x inner PCR primers $P_31, P_32, P_33, P_3x$, and (d) the x inner PCR primers $P_31, P_32, P_33, \ldots P_3x$ are present irreversibly bonded to a solid phase at x spatially separated defined positions, forming a DNA microarray; the method comprising the steps of (1) providing the x PCR primer sets;

(2) performing simultaneous amplification, involving a nested polymerase chain reaction, using said primers in both the solution and the solid phase in order to produce a $P_3$ extension product irreversibly bonded to the solid phase, wherein the x outer PCR primers $P_11$, $P_21, P_12, P_22, P_13, P_23, \ldots P_1x, P_2x$ in the solution are present in a $10^2$ to $10^{12}$-fold excess relative to the x inner PCR primers $P_31, P_32, P_33, \ldots P_3x$ in the solid phase; and (3) ascertaining the presence of the $P_3$ extension product at one or more defined positions of the DNA microarray, wherein the solid phase, to which the x inner PCR primers $P_31, P_32, P_33, \ldots P_3x$ are irreversibly bonded, is a non-porous surface, wherein the non-porous surface is a glass surface and the x inner PCR primers $P_31, P_32, P_33, \ldots P_3x$ are irreversibly bonded to the glass surface via a bifunctional silane that has one, two or three hydrolysable atom(s) or group(s) on the silicon atom.

* * * * *